(12) United States Patent
Vijay et al.

(10) Patent No.: US 7,569,190 B2
(45) Date of Patent: Aug. 4, 2009

(54) MICRO-SAMPLE CUP RACK ADAPTER

(75) Inventors: Tumkur R. Vijay, Newark, DE (US);
David R. Thompson, Kennett Square, PA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 205 days.

(21) Appl. No.: 11/470,138

(22) Filed: Sep. 5, 2006

(65) Prior Publication Data
US 2008/0056956 A1    Mar. 6, 2008

(51) Int. Cl.
B01L 9/06    (2006.01)
G01N 35/02    (2006.01)

(52) U.S. Cl. .................. 422/104; 422/99; 422/102; 422/63; 422/65; 436/43; 206/485; 220/23.91; 220/506

(58) Field of Classification Search ........................ None
See application file for complete search history.

(56) References Cited

U.S. PATENT DOCUMENTS

| | | |
|---|---|---|
| 4,854,479 A | 8/1989 | Callahan et al. |
| 4,944,942 A | 7/1990 | Brown et al. |
| 5,137,693 A | 8/1992 | Mawhirt |
| 5,271,896 A * | 12/1993 | Jakubowicz et al. .......... 422/63 |
| 5,378,433 A | 1/1995 | Duckett et al. |
| 5,687,849 A | 11/1997 | Borenstein et al. |
| 5,985,219 A | 11/1999 | Lind |
| 6,117,391 A | 9/2000 | Mootz et al. |
| 6,274,092 B1 | 8/2001 | Itoh |
| 6,375,027 B1 | 4/2002 | Thomas et al. |
| 6,932,942 B2 | 8/2005 | Itoh |

* cited by examiner

*Primary Examiner*—Jill Warden
*Assistant Examiner*—P. Kathryn Wright
(74) *Attorney, Agent, or Firm*—Leland K. Jordan; Ellen E. Fielitz

(57) ABSTRACT

A small sample cup rack adapter having a spring biased plunger moveably disposed within a generally cylindrical outer body, with the plunger adapted to support a small sample cup within the outer body. After initial contact between an aspiration probe and the bottom of the small sample cup, the probe may be lowered an additional distance, minimizing the "dead volume" of sample.

2 Claims, 8 Drawing Sheets

MICRO-SAMPLE CUP RACK ADAPTER

FIELD OF THE INVENTION

The present invention relates to a system for handling clinical sample containers. In particular, the present invention provides an improved device for introducing patient samples contained in small cups to a probe for aspiration within an automatic clinical analyzer.

BACKGROUND OF THE INVENTION

Various types of analytical tests related to patient diagnosis and therapy can be performed by analysis of a liquid sample taken from a patient's infections, bodily fluids or abscesses. These assays are typically conducted with automated clinical analyzers onto which tubes or vials containing patient samples have been loaded. The analyzer extracts liquid sample from the vial and combines the sample with various reagents in special reaction cuvettes or tubes. Usually the sample-reagent solution is incubated or otherwise processed before being analyzed. Analytical measurements are often performed using a beam of interrogating radiation interacting with the sample-reagent combination to generate turbidimetric, fluorometric, absorption readings or the like. The readings allow determination of end-point or rate values from which an amount of analyte related to the health of the patient may be determined using well-known calibration techniques.

An important contributor to maintaining a high efficiency in throughput of patient samples is the ability to quickly and securely introduce a plurality of samples to the sample testing portion of an analyzer. Patient samples are typically held in a container such as a test tube, and the tubes placed into a sample rack adapted to support multiple sample containers generally in an upright orientation.

The sample rack is usually placed in an input portion of the analyzer and then moved to a location where a portion of the liquid patient sample is extracted, usually by aspiration using a hollow, needle like probe from the sample container for testing in the analyzer, Afterwards, the sample rack may be moved to temporary storage area or to an output portion of the analyzer where the user can conveniently remove the sample rack from the analyzer See for example, Patient samples are known to be provided to such analyzers in a large number of different types of tubes: 13 mm and 16 mm diameter tubes are popular as are "small sample" tubes, sometimes called sample cups, and tubes are also used having varying heights. After being placed on the analyzer, a predetermined, known portion of the original sample is aspirated from the tube and analytical tests conducted thereon. Sample racks with features for accommodating different types of tubes may be found in U.S. Pat. Nos. 5,687,849; 5,378,433; and 4,944,942 and an adapter for accommodating different types of tubes may be found in U.S. Pat. No. 5,985,219, A problem with aspirating sample from a small sample cup arises because the "dead volume" of sample remaining between the bottom of an aspiration probe and the bottom of the small sample cup comprises a large portion of the total sample volume. Uncertainties concerning the exact location of the bottom of the small sample cup prevent positioning the bottom of the probe precisely at the bottom of the small sample cup. Therefore, when a small sample cup is presented to an aspiration probe, the aspiration process is unable to access the total volume of sample within a small sample cup. For obvious reasons, it would be highly desirable to have a device that would automatically enable an aspiration probe to contact the bottom of a small sample cup regardless of the height location of the bottom of that small sample cup.

SUMMARY OF THE INVENTION

The present invention provides a small sample cup rack adapter having a spring biased plunger moveably disposed within a generally cylindrical outer body, with the plunger adapted to support a small sample cup within the outer body. The outer body is sized to be carried in a conventional sample rack that is typically placed within an analyzer and then automatically transported from an input location to a sample aspiration station where sample is aspirated from the small sample cup. The adapted is sized so as to create a small gap between a circumferential flange at the top of the small sample cup and the top of the cylindrical outer body. Due to the biasing action of the spring, after an initial contact between a probe lowered into the small sample cup and the bottom of the small sample cup, the probe may be lowered an additional distance, depressing the moveable plunger, without damaging either the probe or the small sample cup. Consequently, the "dead volume" of sample is minimized as compared to prior art wherein the probe could only be safely lowered to a standard height for all small sample cups, regardless of the exact height location of the bottom of different specific types of small sample cups,

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
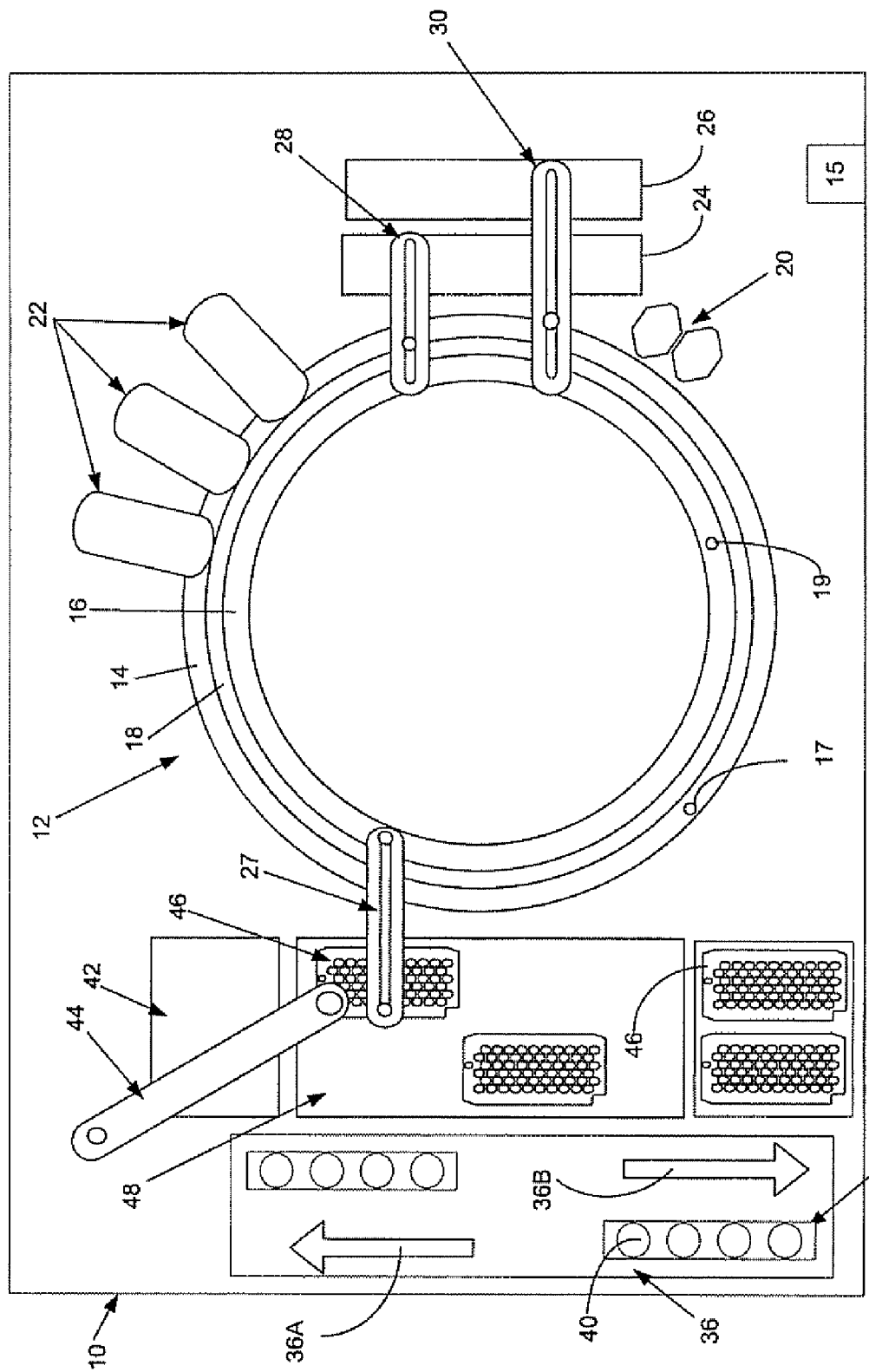
FIG. 1 is a schematic plan view of an automated clinical analyzer in which the present invention may be advantageously employed.

FIG. 1 shows schematically the elements of a conventional automatic chemical analyzer 10 in which the present invention may be advantageously practiced Analyzer 10 comprises a reaction carousel 12 with an outer cuvette circle 14 supporting cuvettes 17 and an inner cuvette circle 16 supporting cuvettes 19, the outer cuvette circle 14 and inner cuvette circle 16 separated by a groove 18. Reaction carousel 12 is rotatable using stepwise movements in a constant direction at a constant velocity, the stepwise movements being separated by a constant dwell time during which dwell time, carousel 12 is maintained stationary and individual computer controlled electro-mechanical devices 20, such as sensors, reagent add stations, mixing stations, and the like, perform the actions required in well known clinical assays. Such devices and their control and operation are described, for example, in U.S. Pat. Nos. 6,573,088; 5,5761215; 5,575,976, and 5,482,861 and the references cited therein.

Temperature-controlled reagent storage areas 24 and 26 store a plurality of reagent containers containing reagents placed into cuvettes 17 and 19 by probes 28 and 30 as necessary to perform a given assay Various assay analyzing means 22 may be located proximate carousels 14 and 16 and are adapted to measure light absorbance in or emission from cuvettes 17 and 19 at various wavelengths, from which the presence of analyte in the sample liquid may be determined using known analytical techniques.

Analyzer 10 is controlled by computer 15 based on software written in a machine language, like that used on the Dimension® clinical chemistry analyzer sold by Dade Behring Inc. of Deerfield, Ill., and widely used by those skilled in the art of computer-based electromechanical control programming to perform assays and related operations given the identity of a patient sample, assay requests, and the like.

Figure 2:
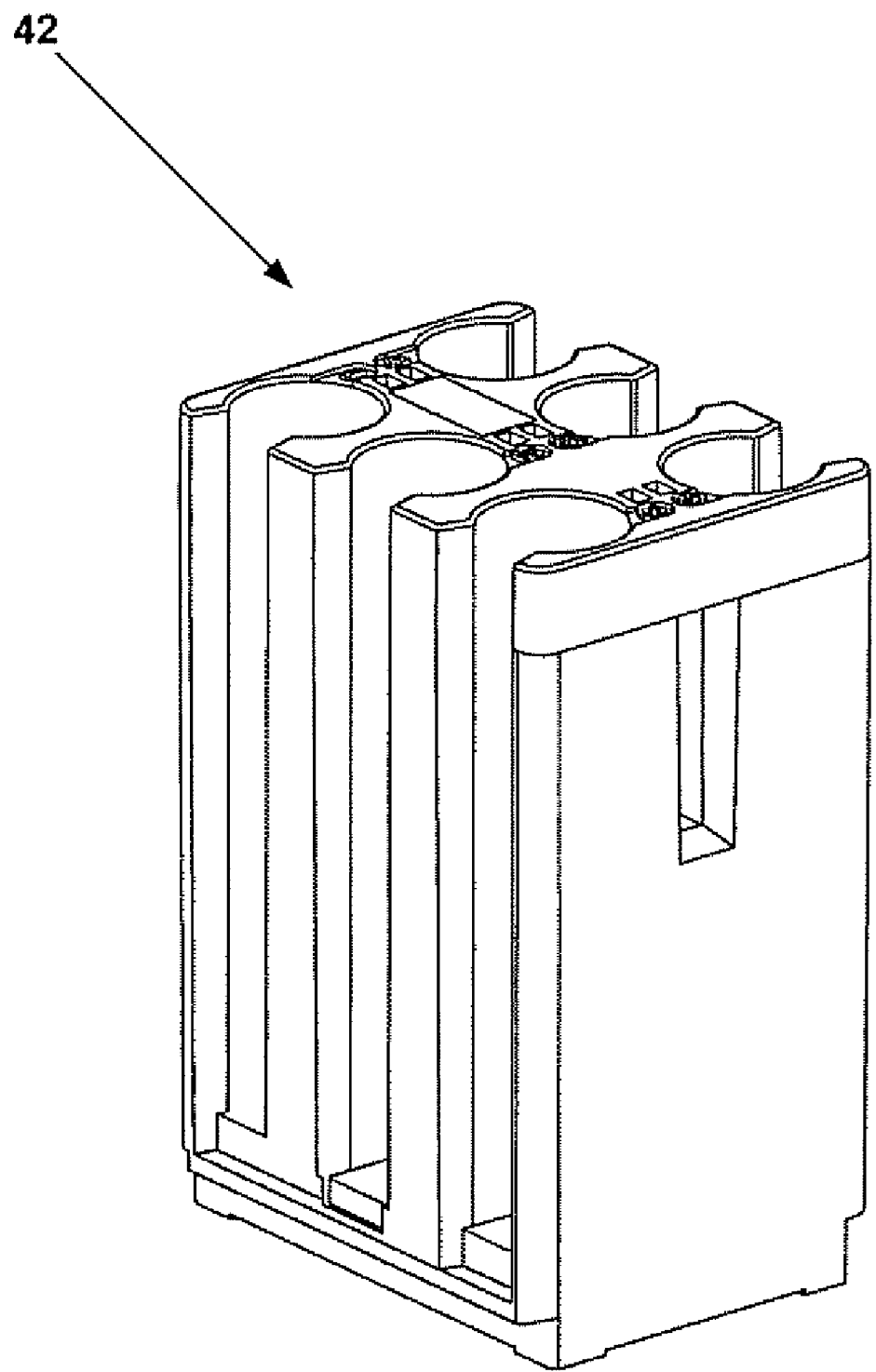
FIG. 2 is a perspective view of a sample rack exemplary for use in an automatic clinical analyzer as seen in FIG. 1.

Incoming samples to be tested are typically contained in sample containers or tubes 40 supported in sample tube racks 42 like seen in FIG. 2 and transportable by a sample tube rack transport system 36 comprising incoming lane 36A and outgoing lane 36B. Aliquot probe 44 is conventionally controlled by computer 15 to aspirate liquid sample from sample tubes 40 and to dispense one or more aliquot portions of the original patient sample into aliquot arrays 46 carried on an aliquot transport system 48 using probe 27 depending on the quantity of sample required to perform the requisite assays and to provide for at least one aliquot portion to be retained by analyzer 10.

Figure 3:
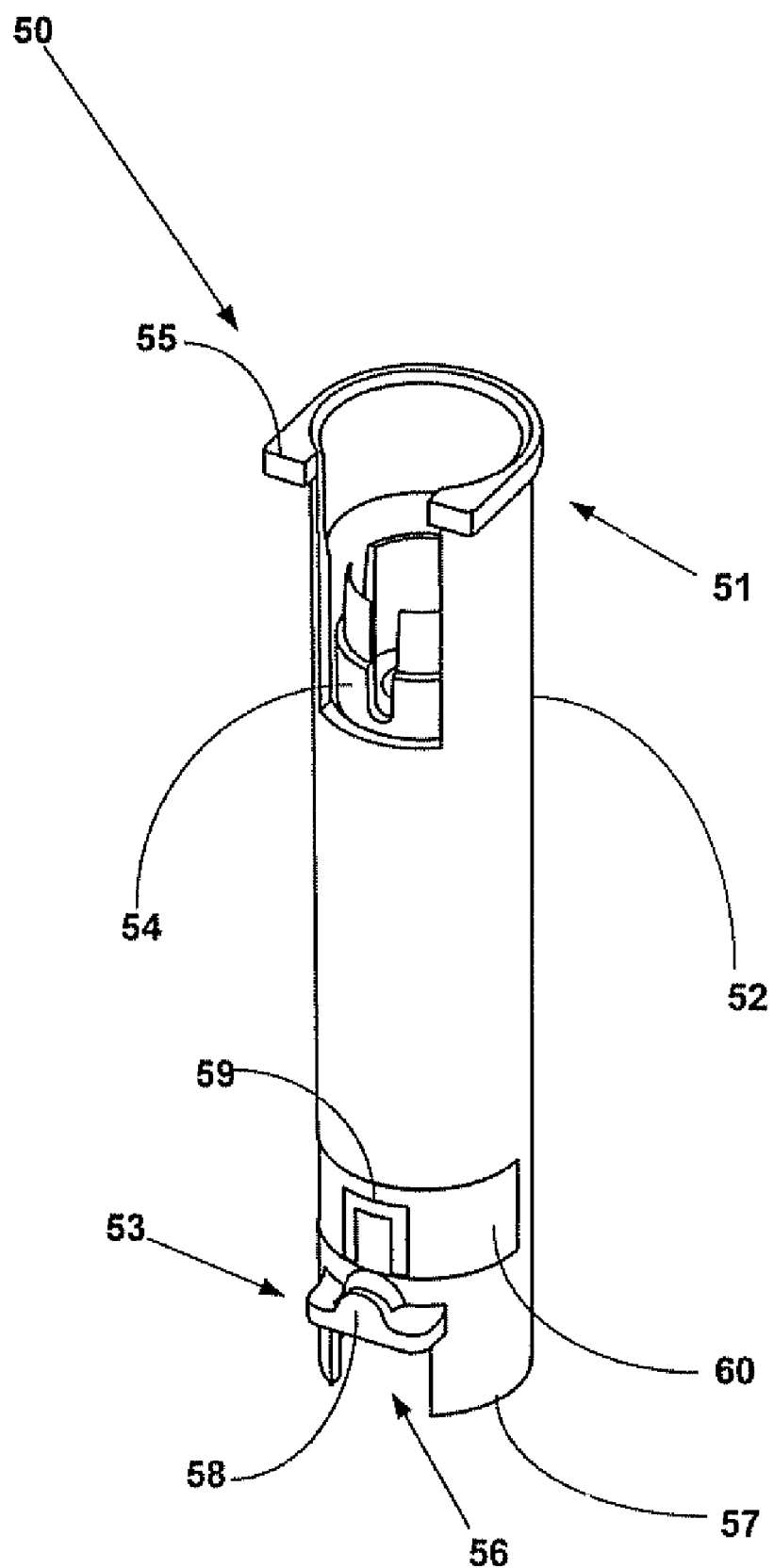
FIG. 3 is a front perspective illustration of the sample cup adapter exemplary of the present invention.
Figure 4:
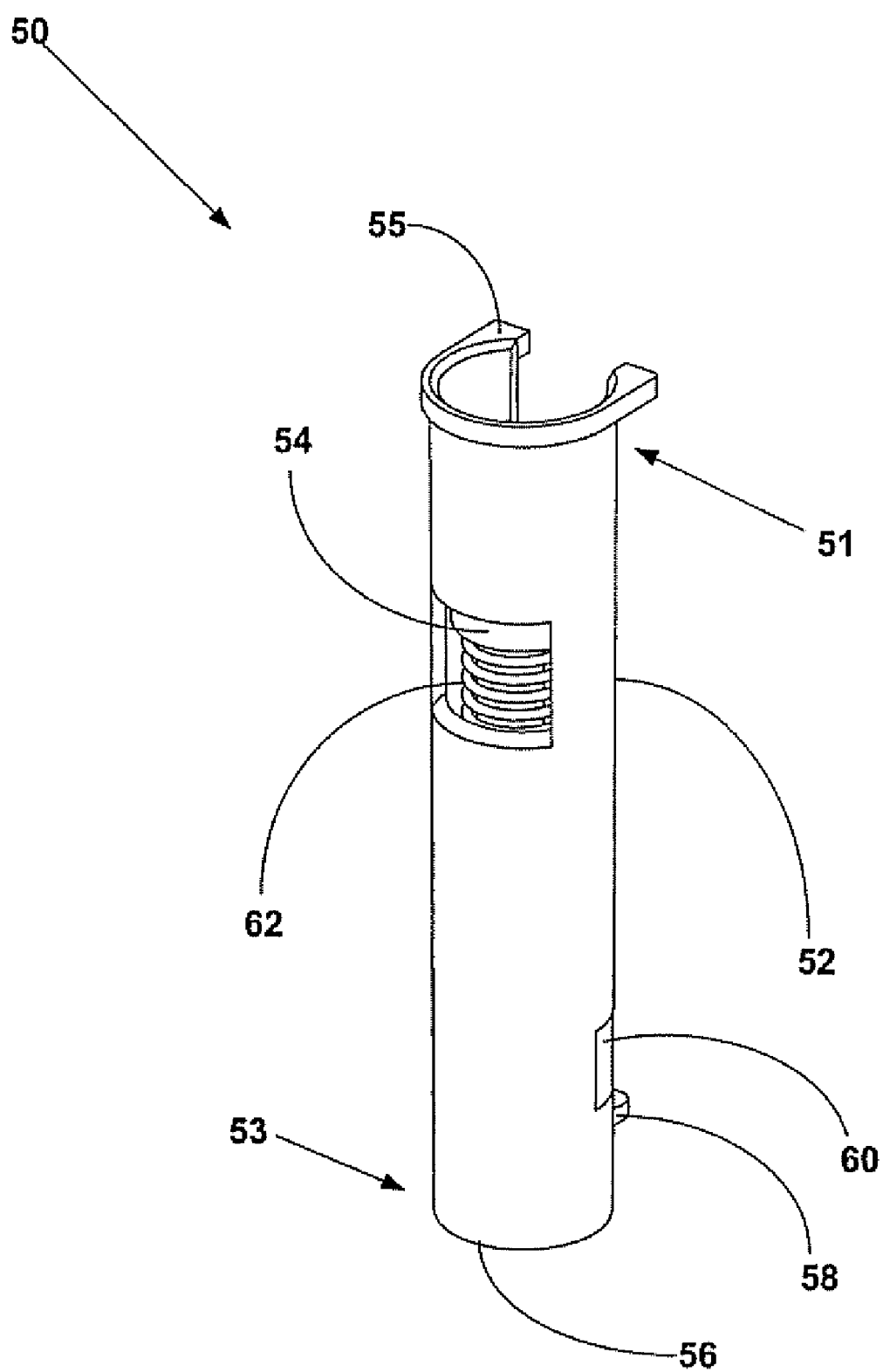
FIG. 4 is a back perspective illustration of the sample cup adapter exemplary of the present invention.

FIG. 3 is a front perspective illustration of the small sample cup adapter 50 exemplary of the present invention, sample cup 50 comprising a generally cylindrical outer body 52 having an open top portion 51 and an open bottom portion 53 at opposite ends thereof A plunger 54 is moveably disposed within outer body 52, plunger 54 adapted to support a small sample cup (not shown) within outer body 52. Plunger 54 is biased upwardly and connected to a compressible spring 62 (seen in FIG. 41 a back perspective illustration of the small sample cup adapter 50) secured within outer body 52 A circumferential flange 55 is formed at the top of outer body 52 and a generally rectangular opening 56 is formed in the bottom 57 of outer body 52. An arrest 58 protrudes from the top of opening 56, arrest 58 and opening 56 adapted to facilitate placement and orientation of adapter 50 within sample rack 42 An identifying mark 59 may be printed upon outer body 52, marking 59 being specifically assigned to a sample tube adapter 50 so as to track a small sample cup within analyzer 10 and to control the mode of aspiration (speed, depth, and the like), Advantageously, marking 59 may be printed on a special background 60 to enhance machine readability.

Figure 5:
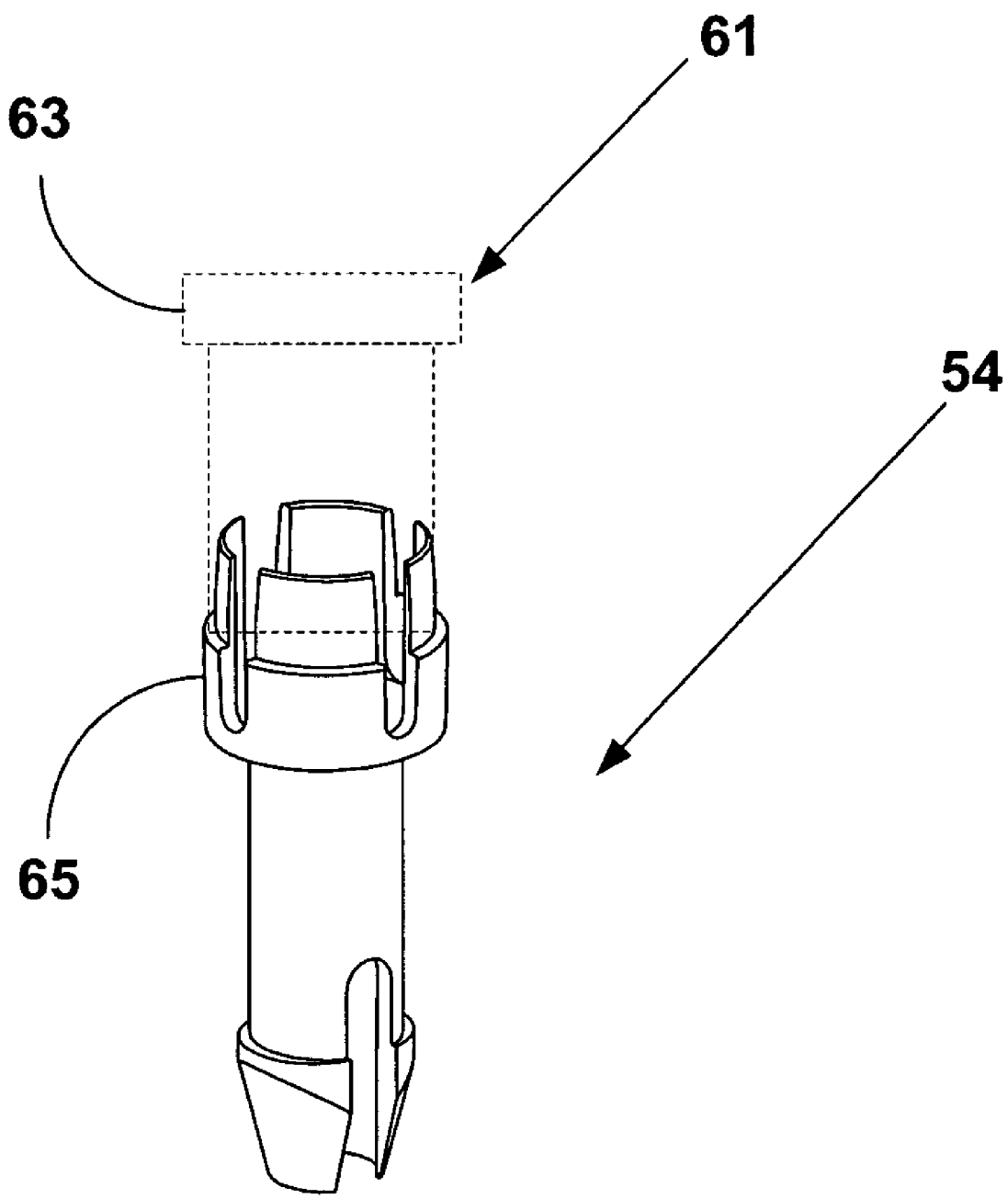
FIG. 5 is a perspective view of a plunger portion of the sample cup adapter exemplary of the present invention.
Figure 6:
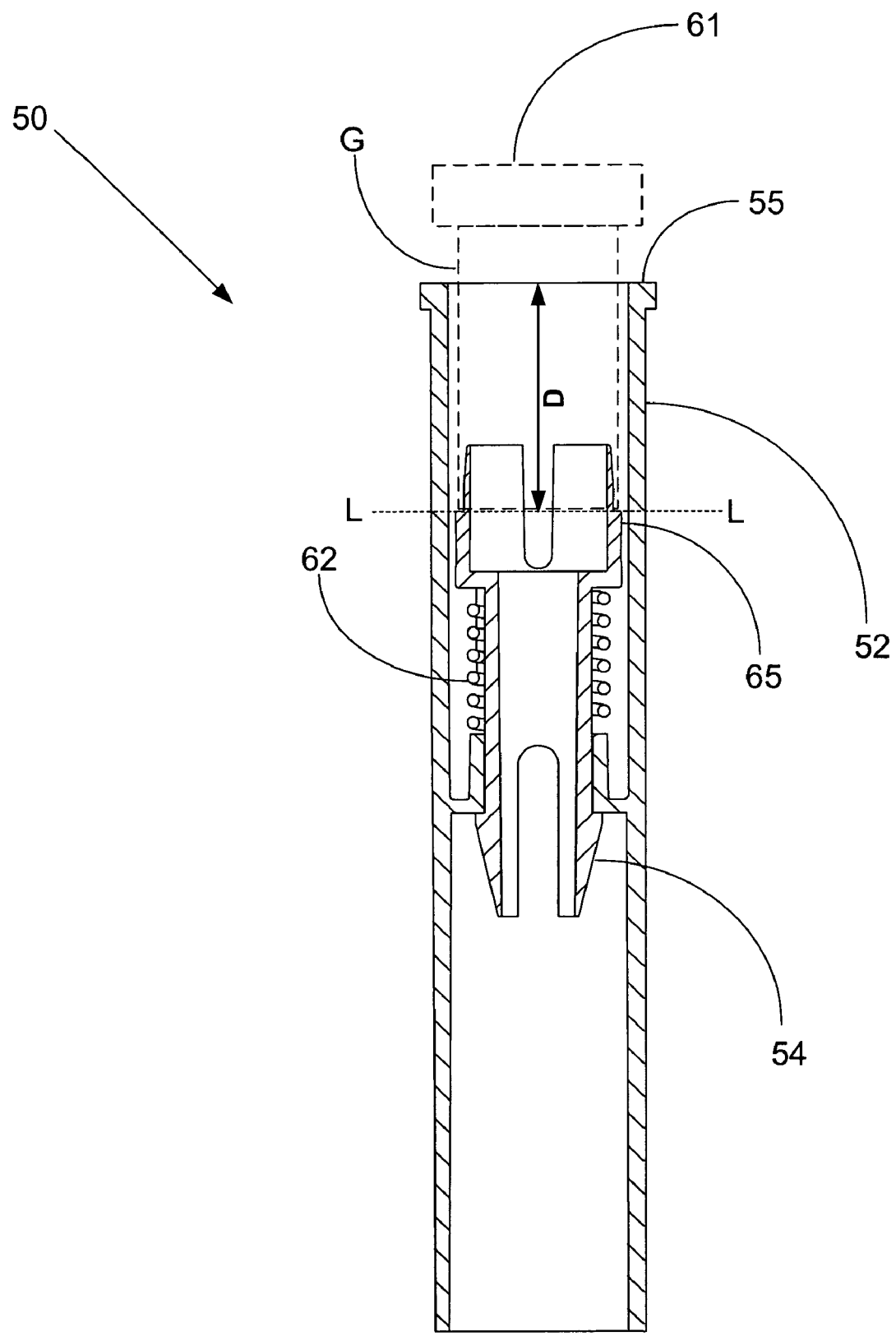
FIG. 6 is a sectional view of the sample cup adapter exemplary of the present invention in an uncompressed condition.

FIG. 5 is a perspective view of plunger 54 with a small sample cup 61 depicted in dashed lines for purposes of illustration. Plunger 54 is seen as having an outer ledge 65 for supporting sample cup 61 within outer body 52 when a small sample cup 61 is placed within adapter 50. An important feature of the small sample cup adapter 50 of the present invention is as the vertical distance D between the top of ledge 65 (dotted line L-L) of plunger 54 and the circumferential flange 55 formed at the top of outer body 52 when spring 62 is in an uncompressed state like seen in the sectional view of FIG. 6. This distance 0 is adjusted so that the distance D between the ledge 65 and the open top portion of the outer body is less than the height of sample cup 61 when spring 62 is in an uncompressed condition thereby forming a small gap G, generally on the order of 2-4 mm, between a circumferential band 63 on sample cup 61 and circumferential flange 55 of outer body 52 when spring 62 is in an uncompressed state. It should be noted that if sample liquid was scheduled to be aspirated from the interior of sample cup 61 by a probe, the distance the probe is lowered into sample cup must be precisely predetermined and controlled in order to minimize so-called "dead volume" or inaccessible sample liquid remaining between the bottom of the probe and the bottom of sample cup 61 even in the instance that the sample cup 61 has a cone-shaped bottom.

Figure 6A:
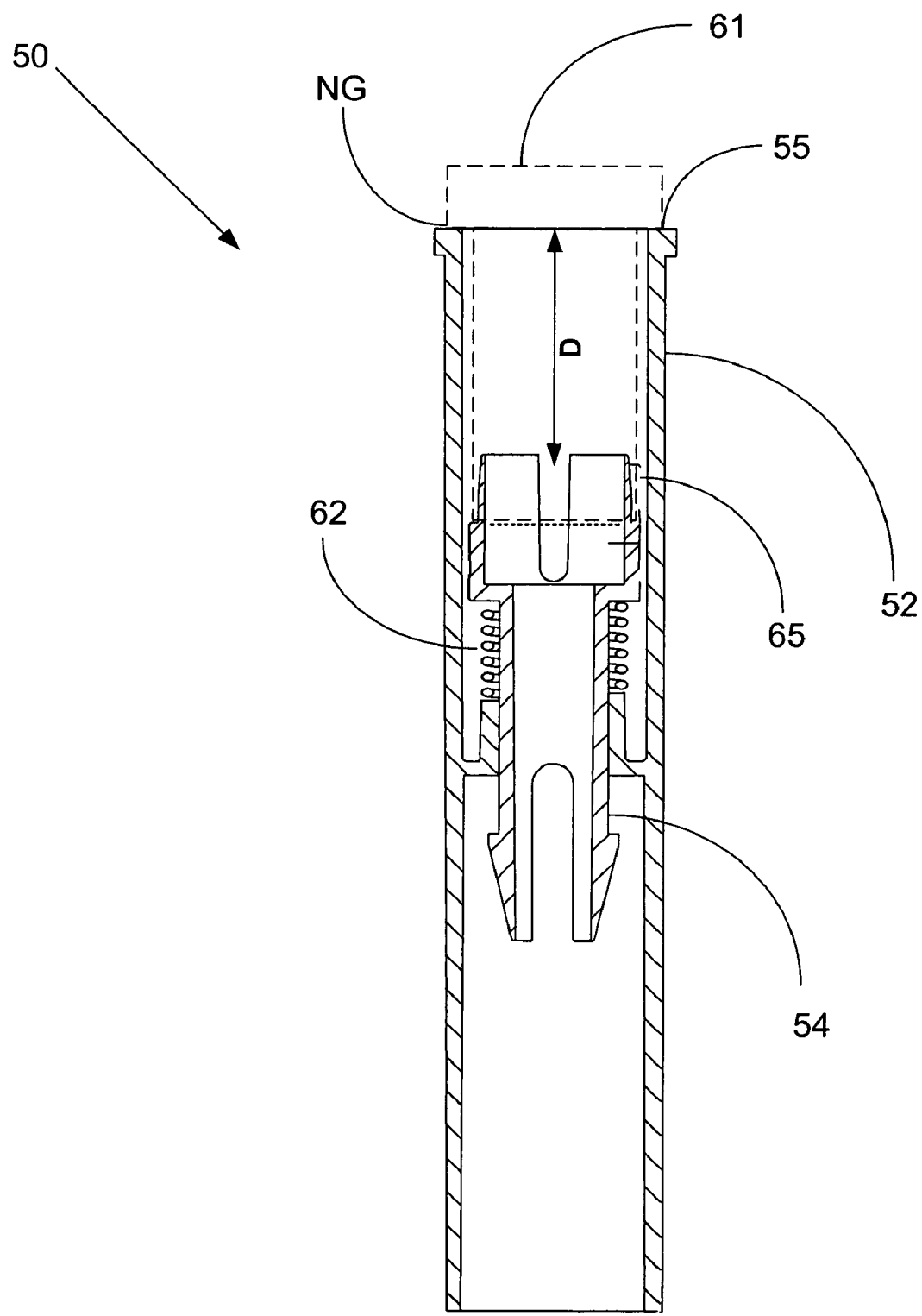
FIG. 6A is a sectional view of the sample cup adapter exemplary of the present invention in a compressed condition; and, FIG. 7 is an exploded assembly view of the sample cup adapter exemplary of the present invention.

FIG. 6A illustrates small sample cup adapter 50 when spring 62 is in an compressed state as a result of being depressed downwards by an aspiration probe (not shown for purposes of simplicity). Sample cup 61 is in contact with the circumferential flange 55 at the top of outer body 52 and there is no gap (NG) therebetween. In this spring 62 compressed condition, the aspiration probe is in physical contact with the bottom of sample cup 61 thereby automatically minimizing "dead volume" sample liquid without requiring intricate measurements and mechanisms.

Figure 7:
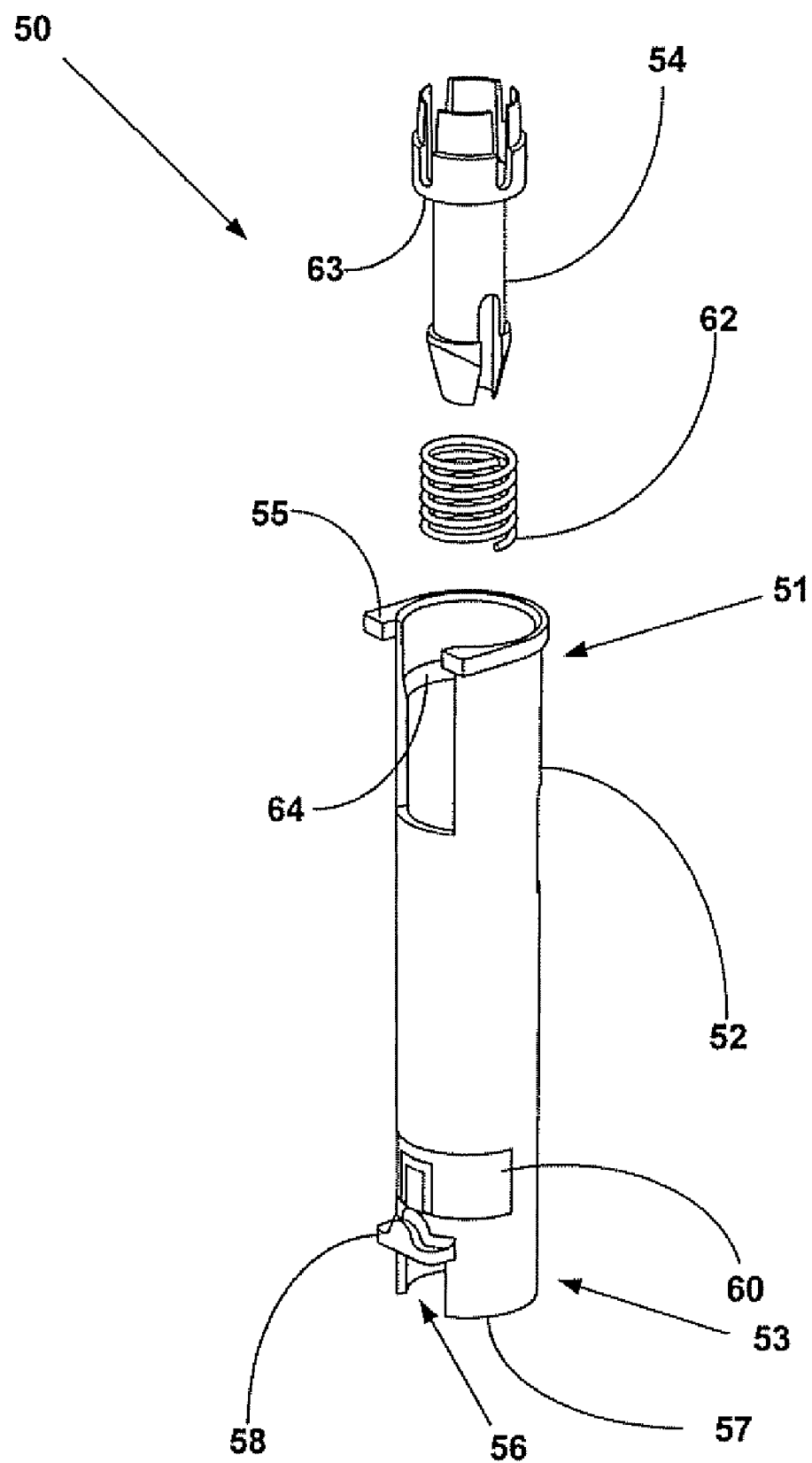

FIG. 7 is an exploded assembly view of the sample cup adapter 50 showing an outermost flange 63 formed on plunger 54 and sized to mate with shoulder 64 formed on the inside of outer body 52, thereby to prevent plunger 54 from being pushed below the intersection of flange 63 formed and shoulder 64.

In use, when a small sample cup contains patient sample to be analyzer, an operator places sample cup 61 within small sample cup adapter 50 forming a small gap between circumferential flange 55 at the top portion 51 of cylindrical outer body 52. Due to the biasing action of spring 62, after an initial contact between a probe lowered into the small sample cup and the bottom of the small sample cup 61, the probe may be lowered until band 63 of sample cup 61 contacts flange 55, depressing moveable plunger 54, without damaging either the probe or the small sample cup 61 Consequently, the "dead volume" of sample is minimized as compared to prior art wherein the probe could only be safely lowered to a standard height for all small sample cups 61, regardless of the exact height location of the bottom of different specific types of small sample cups 61.

It should be readily understood by those persons skilled in the art that the present invention is susceptible of a broad utility and application Many embodiments and adaptations of the present invention other than those herein described, as well as many variations, modifications and equivalent arrangements will be apparent from or reasonably suggested by the present invention and the foregoing description thereof, without departing from the substance or scope of the present invention.

Accordingly, while the present invention has been described herein in detail in relation to specific embodiments, it is to be understood that this disclosure is only illustrative and exemplary of the present invention and is made merely for purposes of providing a full and enabling disclosure of the invention The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. An article of manufacture comprising in combination:
    an open sample cup for holding a volume of liquid and having a height;

a sample cup adapter for holding said sample cup the adapter comprising a generally cylindrical outer body having an open top and an open bottom portion at opposite ends thereof and a shoulder formed on the upper inside of the outer body;

a plunger moveably disposed within said outer body, the plunger having an outer ledge for supporting the sample cup within the outer body when a sample cup is placed within the adapter;

a compressible spring disposed within the outer body and positioned between the shoulder of the adapter and the ledge of the plunger so as to bias the plunger in a direction towards the open top of the adapter, wherein the vertical distance between the top of outer ledge of the plunger and the open top of the outer body is less then the height of the sample cup when the spring is in an uncompressed state.

2. The article of manufacture of claim 1 wherein the sample cup is in contact with the top of the outer body when the spring is in a compressed state.

* * * * *